(12) United States Patent
Fortuna et al.

(10) Patent No.: US 11,199,531 B2
(45) Date of Patent: Dec. 14, 2021

(54) DIAGNOSTIC SUPPORT FOR SKINS AND INSPECTION METHOD OF SKIN

(71) Applicant: Epica International, Inc., San Clemente, CA (US)

(72) Inventors: Damiano Fortuna, Rignano Sull'Arno (IT); Leonardo Manetti, Montevarchi (IT); Dario Brugnoli, Piombino (IT); Giulio Raimondi, Pisa (IT); Daniele Pasciuto, Gaeta (IT); Giovanni De Santis, Pisa (IT); Corrado Taviani, Fucecchio (IT)

(73) Assignee: Epica International, Inc., San Clemente, CA (US)

( * ) Notice: Subject to any disclaimer, the term of this patent is extended or adjusted under 35 U.S.C. 154(b) by 68 days.

(21) Appl. No.: 16/098,846

(22) PCT Filed: May 5, 2017

(86) PCT No.: PCT/IB2017/052619
§ 371 (c)(1),
(2) Date: Nov. 2, 2018

(87) PCT Pub. No.: WO2017/191602
PCT Pub. Date: Nov. 9, 2017

(65) Prior Publication Data
US 2019/0145949 A1    May 16, 2019

(30) Foreign Application Priority Data
May 5, 2016   (IT) .......................... UA2016A003175
May 11, 2016  (IT) .......................... US2016A003360

(51) Int. Cl.
C14B 1/62     (2006.01)
C14B 17/00    (2006.01)
(Continued)

(52) U.S. Cl.
CPC .............. *G01N 33/447* (2013.01); *C14B 1/62* (2013.01); *C14B 17/16* (2013.01); *G01N 23/046* (2013.01);
(Continued)

(58) Field of Classification Search
None
See application file for complete search history.

(56) References Cited

U.S. PATENT DOCUMENTS 6,157,730 A * 12/2000 Roever ................... G01N 21/89
                                                    382/110
6,599,247 B1 *  7/2003 Stetten .................... A61B 8/00
                                                    128/916
(Continued)

OTHER PUBLICATIONS

Moasheri et al., "A New Voting Approach to Texture Defect Detection Based on Multiresolutional Decomposition," World Academy of Science, Engineering and Technology International Journal of Computer and Information Engineering, vol. 5 No. 1 (Year: 2011).*

*Primary Examiner* — Soo Shin
(74) *Attorney, Agent, or Firm* — Steptoe & Johnson LLP; Robert Greenfeld

(57) ABSTRACT

A diagnostic support for a skin includes a radio-transparent structure that defines a folding surface of the skin and on which the skin may be stretched and consequently folded, thereby defining folded, mutually superimposed portions spaced apart from each other. The support may be used for radiographic inspection of a folded animal skin.

12 Claims, 5 Drawing Sheets

(51) Int. Cl.
  *G01N 23/046* (2018.01)
  *G01N 33/44* (2006.01)
(52) U.S. Cl.
  CPC . *G01N 2223/309* (2013.01); *G01N 2223/612* (2013.01); *G01N 2223/646* (2013.01)

(56) References Cited

U.S. PATENT DOCUMENTS

| | | | | |
|---|---|---|---|---|
| 2009/0273669 | A1* | 11/2009 | Wertsman | G06T 7/0004 348/87 |
| 2011/0299653 | A1* | 12/2011 | Mishra | G01N 23/02 378/9 |
| 2012/0307969 | A1* | 12/2012 | Kraus-Guentner | C14B 17/16 378/58 |
| 2017/0309063 | A1* | 10/2017 | Wang | G01N 21/4795 |
| 2018/0120243 | A1* | 5/2018 | Yashima | G01N 23/046 |
| 2021/0072165 | A1* | 3/2021 | Kaneko | G01N 23/18 |

* cited by examiner

DIAGNOSTIC SUPPORT FOR SKINS AND INSPECTION METHOD OF SKIN

CROSS-REFERENCE TO RELATED APPLICATIONS

This application is a National Stage Filing based on and claiming priority from International Application No. PCT/162017/052619, filed May 5, 2017, which claims priority from Italian Patent Application Nos. UA2016A003175, filed May 5, 2016, and UA2016A003360, filed May 11, 2016, each of which is incorporated by reference in its entirety.

FIELD OF THE INVENTION

The present invention relates to a diagnostic support for skins and a method of skin inspection. In particular, the present invention relates to a support and a method allowing an acquisition which facilitates the identification of defects in skins, and in particular in leather.

BACKGROUND

As is known, skins of animals usually selected from cattle, sheep, goats, pigs, horses, and more rarely deer, kangaroos, or ostriches are often used for the production of car upholstery, upholstered furniture, clothing, shoes, and many other items. Preferably, the animals used are selected from cattle and horses. The skins, prior to cutting, and therefore prior to the manufacture of the object, are subjected to an analysis process to identify possible defects that, if not removed, could cause major imperfections in the object. Therefore, before processing, an inspector visually checks and marks the defects on the skin with a color that, by being read by a camera, allows a computer to easily locate the defects present on the skin.

The above mentioned prior art has a few major drawbacks. A first major drawback is that the inspector, despite care and accuracy, is not able to detect all the defects or to properly evaluate their extent, leading to the discarding of skins erroneously judged non-compliant or to the approval of skins that, instead, should be discarded. Another major drawback is the impossibility of having a uniformity of judgment due to fatigue of the inspector and non-uniformity of judgment among the various inspectors. In fact, an important drawback is that, once the image has been obtained, it is very difficult to accurately locate the defects in the skin found in the acquired image, which results in cutting portions that are much larger than the defect. Thus, a drawback is that these discarded parts increase the final price of the manufacturing, and therefore of the purchased skins. A further drawback is the use of non-compliant skins, with consequent manufacture of low quality products.

SUMMARY

In this context, the technical task of one embodiment of the present invention is to devise a diagnostic support for skins and a method of skin inspection, which are capable of substantially obviating the above-mentioned drawbacks. Within the scope of this technical task, a major object of one embodiment of the invention is to obtain an inspection method and a diagnostic support, which make it possible to identify and evaluate all the skin defects in a simple and quick manner. An object of one embodiment of the invention is to provide a method and a support that minimize the discarded parts of the skin and therefore reduce the overall costs and the wastage of skins.

BRIEF DESCRIPTION OF THE DRAWINGS

The various embodiments of the invention will now be described in the following detailed description, with reference to the attached drawings, in which:

FIG. 1b shows the use of the diagnostic support of FIG. 1a;

DETAILED DESCRIPTION

Figure 1A:
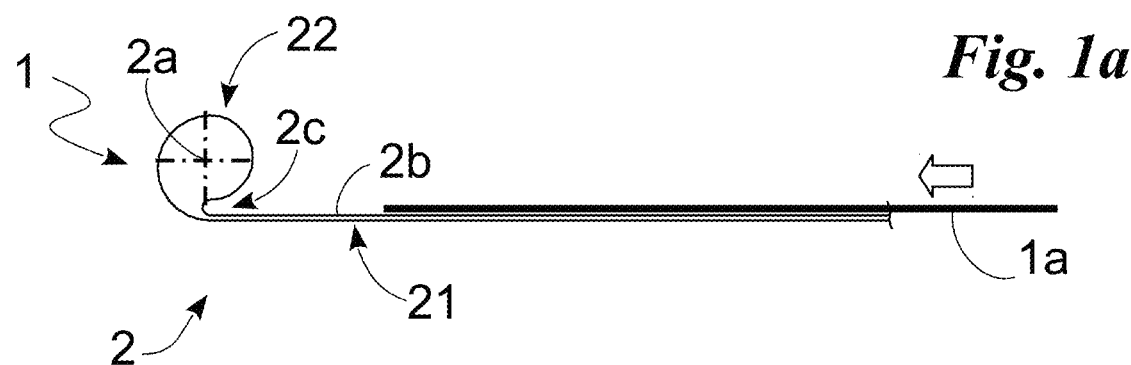
FIG. 1a shows a diagnostic support for skins according to an embodiment of the present invention.

In this document, the measures, values, shapes and geometric references (such as perpendicularity and parallelism), when associated with words like "about" or other similar terms such as "almost" or "substantially," are to be understood to the extent of measurement errors or inaccuracies due to production and/or manufacturing defects and, especially, to the extent of a slight difference from the value, the measure, the shape, or the geometric reference with which it is associated. For example, these terms, if associated with a value, preferably indicate a difference not exceeding 10% of the value itself.

Furthermore, when used, terms such as "first," "second," "higher," "lower," "main," and "secondary" do not necessarily identify an order, a priority relationship, or a relative position, but can simply be used to distinguish more clearly the different components from each other.

Unless otherwise specified, as is apparent from the following discussion, terms such as "treatment," "data processing," "determination," "calculation," or the like, are understood to refer to the action and/or processes of a computer or similar electronic computing device which manipulates and/or transforms data represented as physical, such as electronic sizes of registers of a computer system and/or memories, into other data similarly represented as physical quantities in computer systems, registers or other storage, transmission or information display devices.

With reference to the aforementioned figures, the diagnostic support for skins according to the invention is designated as a whole by the reference numeral 1 and is adapted to allow the execution of an inspection of a skin 1a in an inspection apparatus. The skin 1a is from an animal suitably selected from cattle, sheep, goats, pigs or horses. When stretched, it may have a width at least equal to 2 m and, on average, of at least about 3 m. The skin 1a, when stretched, defines an exposed surface, a support surface of the skin 1a opposite to the exposed surface, and a lateral surface defining the profile/perimeter of the skin 1a and connecting the exposed surface to the support surface.

The inspection apparatus comprises an imaging device 10 adapted to image the skin 1a stretched and/or folded by the diagnostic support 1 described below. The term "imaging" identifies an image, which is three-dimensional or two-dimensional and reproduces at least the internal structure of the skin 1*a* not visible from the outside. The imaging device 10 can be radiological, i.e. adapted to provide a radiological (radiographic, fluoroscopic, or tomographic) image, and precisely a tomographic device adapted to provide a tomography of the skin 1*a*.

An example of the imaging device 10 is described in WO2015/112425, hereby incorporated by reference, in paragraphs [0009]-[0092] and in FIGS. 1-8. Another example is presented in WO2016/009316, hereby incorporated by reference, from page 2, line 8 to page 59, line 23 and in FIG. 1*a*-5.

Figure 1B:
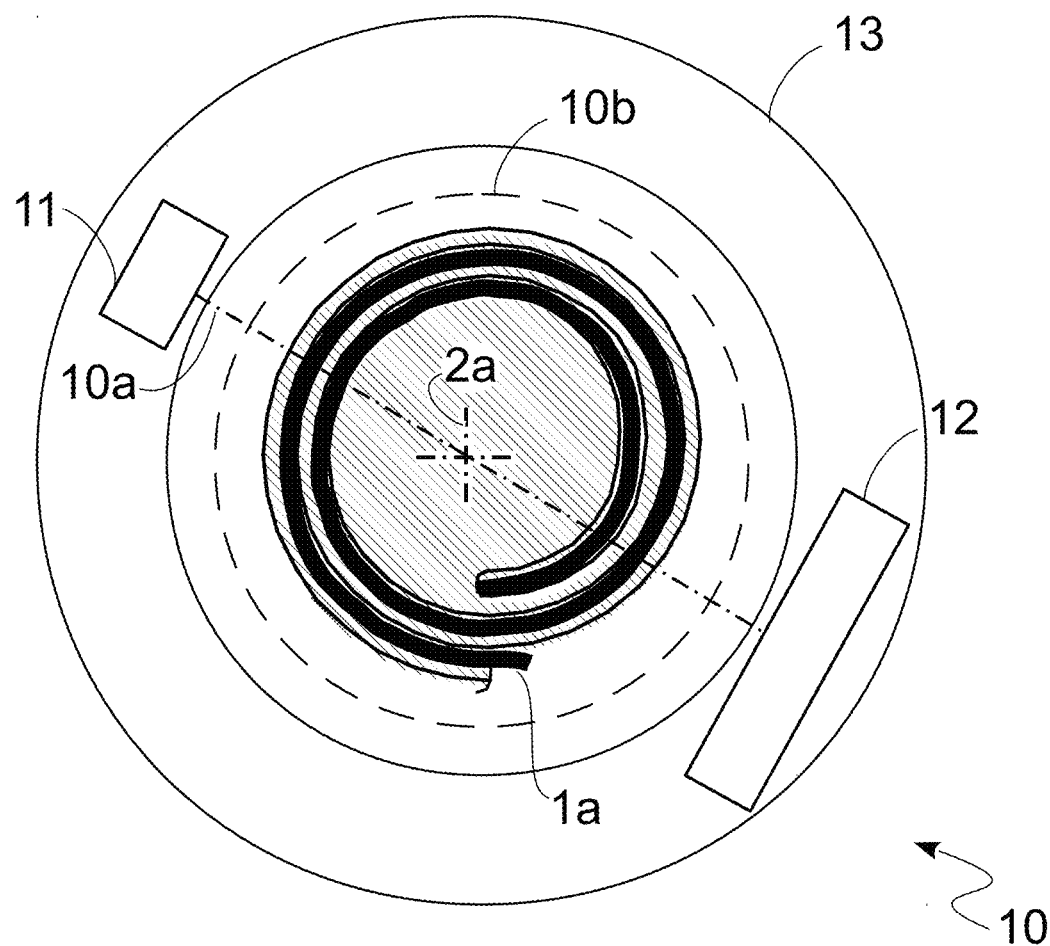

Imaging device 10, as shown in FIG. 1*b*, defines an emission axis 10*a* and an FOV 10*b* (acronym for "Field Of View," the visual field) identifying the acquisition field of the device 10. The FOV 10*b* defines an isocentre, i.e. an axis suitably substantially perpendicular to the emission axis and along which the FOV 10*b* extends, preferably in a barycentric position. The FOV 10*b* usually has a cylindrical shape with the isocentre as its axis. It can extend to the skin 1*a* and in detail it can have a diameter of less than the width of the skin 1*a* when stretched, i.e. flat. Precisely, the diameter of the FOV 10*b* is substantially less than 1.5 m, in detail less than 1 m, in detail less than 0.7, m and preferably substantially comprised between 0.3 m and 0.4 m.

The imaging device 10 may comprise a source 11 adapted to emit (preferably X-rays) along the emission axis 10*a* conveniently perpendicular and incident to the isocentre and a detector 12 adapted to perform one or more acquisitions of the skin 1*a* by receiving said emission after it has crossed the FOV 10*b*, and therefore at least part of the diagnostic support 1 and of the skin 1*a*. The imaging device 10 may comprise a rotating member that is adapted to simultaneously rotate the source 11 and the detector 12 around the FOV 10*b*, defining a rotation axis substantially coincident with the isocentre, and a reconstruction unit capable of imaging according to said acquisitions. The imaging device 10 may comprise a gantry 13 enclosing the FOV 10*b* and defining a volume for housing the source 11, the detector 12, and suitably the rotating member. As an alternative to the gantry 13, the device 10 can provide a known C-arm.

Additionally, the imaging device 10 may comprise a moving apparatus adapted to translate the gantry 13 or the C-arm along the isocentre. The inspection apparatus may comprise at least one recording unit adapted to provide an image of the skin surface 1*a*, i.e. an image reproducing substantially the sole outer profile of the skin 1*a*. The recording unit and the imaging device 10 may image the skin 1*a* at the same time and/or at different times. The recording unit is adapted to provide an image of the skin 1*a* stretched and/or folded by the diagnostic support 1 described below. It is suitable to record at least part of the exposed surface, and preferably the entire exposed surface, with the recording axis suitably almost perpendicular to the exposed surface. The recording unit may provide an optical image of the skin 1*a* and therefore comprise at least one camera. Alternatively, it may comprise one or more laser scanner sensors (also called 3D lasers) adapted to detect the three-dimensional pattern of the skin 1*a*.

The inspection apparatus may comprise an evaluation module adapted to allow inspection of the skin 1*a* based on the imaging and the superficial image. The evaluation module is in data connection with the imaging device and the recording unit so as to receive the images obtained therefrom. It can comprise a control board adapted to analyze the images and, suitably, a screen designed to display the results of the inspection. The evaluation module can comprise a memory comprising several acquired images and a defects database, described below, for each skin 1*a*.

The inspection apparatus may comprise at least one marker suitable to be bonded to the skin 1*a* conveniently at the exposed surface. The inspection apparatus may comprise at least two markers and, in detail, three markers. The marker can be optical, i.e. visible to an optical camera, or radio-opaque, i.e. visible during the radiological acquisition, or thermal and therefore visible with a thermographic camera.

In order to be visible in the superficial image, the marker can be of the optical type (for example colored differently from the skin 1*a*) so as to be visible in the optical image. Alternatively, the marker may have a peculiar thickness easily identifiable through the laser scanner. In order to be visible by imaging, the marker may have a different absorption behavior in the imaging with respect to the skin 1*a*. It can therefore be radio-opaque or alternatively radio-transparent and for example identifiable in a hole made in the skin 1*a* and preferably characterized by a peculiar section.

Preferably, the marker is both optical and radio-opaque and thus visible in the imaging as well as in the superficial image. It may have a peculiar shape/profile easily identified both in the imaging and in the superficial image, and therefore be innovatively used for reference between the imaging and the superficial image as described below. In some cases, the marker may comprise a chessboard alternating radio-transparent elements recordable, preferably exclusively, by an optical camera, and radio-opaque elements recordable by an imaging device and suitably by an optical camera.

Finally, the inspection apparatus may comprise a device for removing the defects from the skin 1*a*, for example by cutting the skin 1*a*.

The imaging device and the recording unit, the at least one marker, and, if present, the removal device can be structurally mutually associated so as to uniquely define a position relative to each other, and preferably allow the apparatus to acquire images, inspect the skin 1*a*, and possibly remove the defects without moving the skin 1*a*.

The diagnostic support 1 is adapted to be at least partially included in the FOV 10*b*, i.e. between the source 11 and the detector 12. The diagnostic support 1 may comprise a radio-transparent structure 2 defining a longitudinal axis 2*a* and suitable to be introduced in the FOV 10*b* by placing the longitudinal axis 2*a* preferably substantially parallel and, in detail, coincident with the isocentre. The radio-transparent structure 2 is adapted to fold a skin 1*a* so that it takes on a size smaller than the diameter of the FOV 10*b* and is thus at least partly included in the FOV 10*b*. In detail, it is designed to fold the skin 1*a*, thus defining folded portions of the skin 1*a* normally superimposed along the longitudinal axis 2*a*. More in detail, the structure 2 is suitable to position itself between the folded portions of the skin 1*a*, thus spacing the folded portions apart, preferably at the same distance from each other. The folded portions can therefore be superimposed along the emission axis 10*a*.

The radio-transparent structure 2 is adapted to define at least one folding surface 2*b* of the skin 1*a* suitably designed to position itself between the folded portions, thus spacing them apart, preferably at the same distance from each other. The at least one folding surface 2*b* is adapted to fold the skin 1*a* defining a radius of curvature substantially equal to at least 5 cm, and in detail equal to 10 cm, so as to avoid the formation of folds or other defects on the skin 1*a*. It extends substantially parallel to the longitudinal axis 2*a*.

A few preferred embodiments of a radio-transparent structure 2 are described below in a non-limiting way. A first preferred embodiment of the radio-transparent structure 2 defining a single folding surface 2b is shown in FIGS. 1a and 1b. This structure 2 comprises a flexible plate 21 defining the folding surface 2b. The flexible plate 21 is adapted to allow at least part of the skin 1a, and more precisely the entire skin 1a, to be placed on said folding surface 2b and to curl up on itself around the longitudinal axis 2a, thus folding the skin 1a into a spiral shape and positioning itself between the folded portions. The flexible plate 21 has a thickness, calculated perpendicular to the folding surface 2b, which is substantially constant, and in detail substantially equal to 0.5 cm. The folding surface 2b, and thus the flexible plate 21, have a length, measured along the longitudinal axis 2a, at least equal to 2 m, and precisely equal to 3 m. The folding surface 2b, and thus the flexible plate 21, have a width, calculated perpendicular to the longitudinal axis 2a, at least equal to 2 m, and precisely equal to 3 m.

The plate 21 is made of a radio-transparent material such as polyurethane foam. In this first preferred embodiment, the radio-transparent structure 2 may comprise a base body 22 on which the plate 21 (see FIG. 1b), and thus the skin 1a, is wound, defining an axis substantially extending almost parallel to the longitudinal axis 2a. The base body 22 is made of a radio-transparent material such as polyurethane foam. It is integral with the flexible plate 21 at one of its edges parallel to the longitudinal axis 2a. Preferably, the base body 22 and the flexible plate 21 are bonded to each other by placing the surface 2b substantially tangent to the outer surface of the base body 22. More preferably, the structure 2 defines a channel 2c to fit the skin 1a between the base body 22 and the plate 21 parallel to the longitudinal axis 2a. Conveniently, the base body 22 and the flexible plate 21 are in one piece. The base body 22 has a circular section, perpendicular to the longitudinal axis 2a, with a diameter suitably at least equal to 5 cm, and in detail equal to 10 cm.

Finally, in this preferred embodiment, the diagnostic support 1 may comprise fastening means, such as one or more elastic bands or clips, adapted to lock the flexible plate 21, and hence the skin 1a, wound on the base body 22 (FIG. 1b). The fastening means are made of polyurethane foam or of a radio-transparent material.

In other preferred embodiments, the radio-transparent structure 2 defines several folding surfaces 2b mutually alternated on opposite sides with respect to a longitudinal plane 2d crossing the longitudinal axis 2a and, suitably, the isocentre. Longitudinal plane 2d can, for example, be parallel (FIGS. 2 and 3c) or perpendicular (FIG. 4b) to the gravitational gradient. Alternatively, it may have any inclination with respect to the gravitational gradient.

The folding surfaces 2b may be axially spaced apart from each other, thereby avoiding mutual contact between the folded portions of the skin 1a. Advantageously, the folding surfaces 2b are axially equally spaced apart from each other so that the folded portions of the skin 1a are equally spaced apart from each other. More advantageously, the folding surfaces 2b are parallel to each other and axially equally spaced apart so that the folded portions of the skin 1a are parallel to each other and equally spaced apart from each other. It should be noted that terms such as axially and axial identify, throughout the document, a direction perpendicular to the longitudinal axis 2a and along the longitudinal plane 2d.

Figure 2:
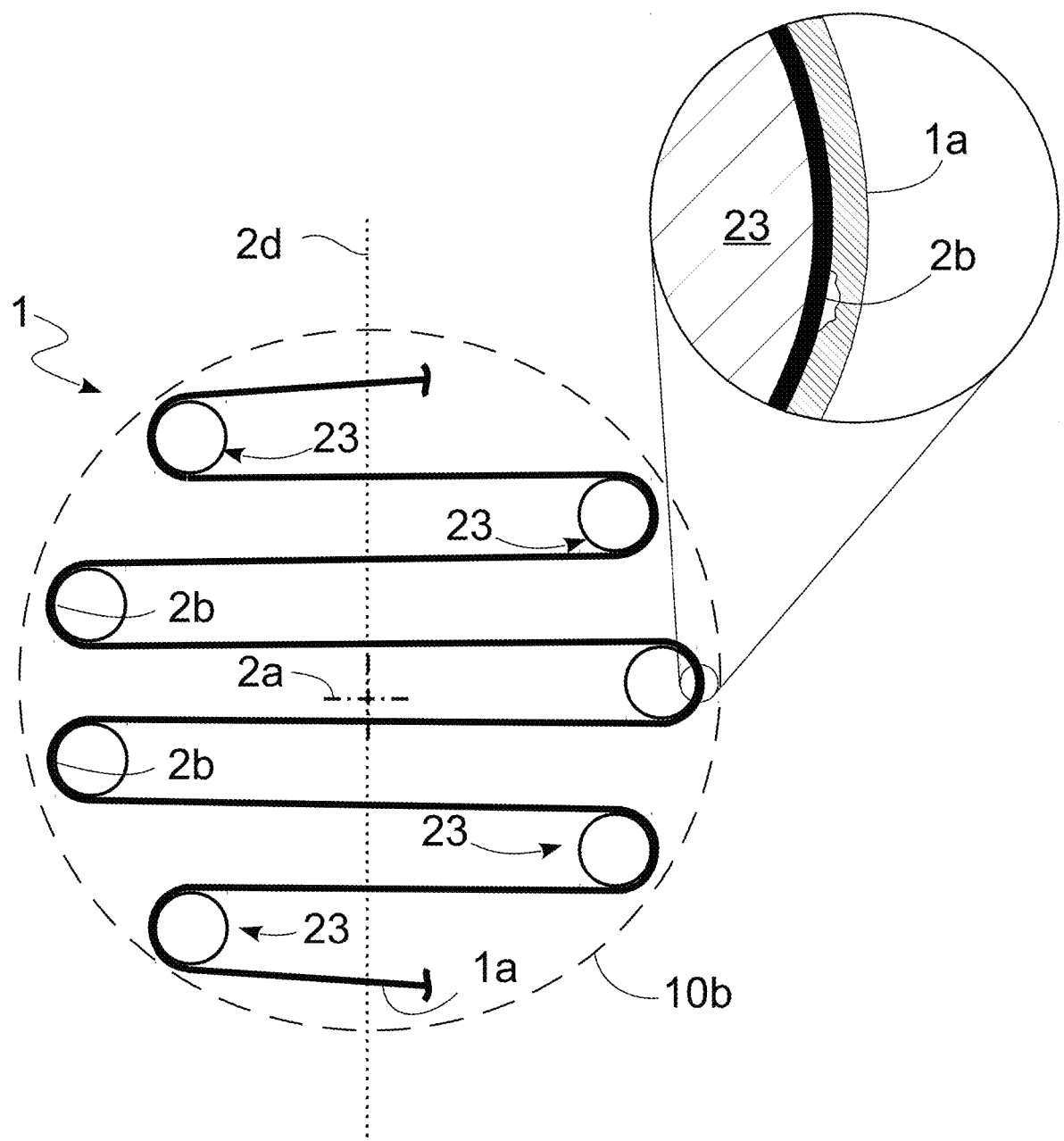
FIG. 2 shows a further diagnostic support for skins according to an embodiment of the present invention.

An example of a radio-transparent structure 2 is shown in FIG. 2 showing a second preferred embodiment. In this case, the radio-transparent structure 2 may comprise sections 23, each of which defines a folding surface 2b. The sections 23 and the surfaces 2b are mutually alternated on opposite sides with respect to the longitudinal plane 2d and axially spaced from each other, thus defining mutually separate folded portions. Advantageously, the sections 23 are axially equally spaced apart. More advantageously, they are equidistant from the longitudinal axis 2a. The sections 23 may be substantially parallel to the longitudinal axis 2a. They may have a length, measured along the longitudinal axis 2a, at least equal to that of the skin 1a, and in detail equal to 3 m. The sections 23 may have a circular section with a diameter suitably at least equal to 5 cm, and in detail equal to 10 cm. The sections 23 are made of a radio-transparent material such as polyurethane foam. Finally, the diagnostic support 1 may comprise a frame suitable to support the sections 23 and attachable to the imaging device 10.

Figure 3A:
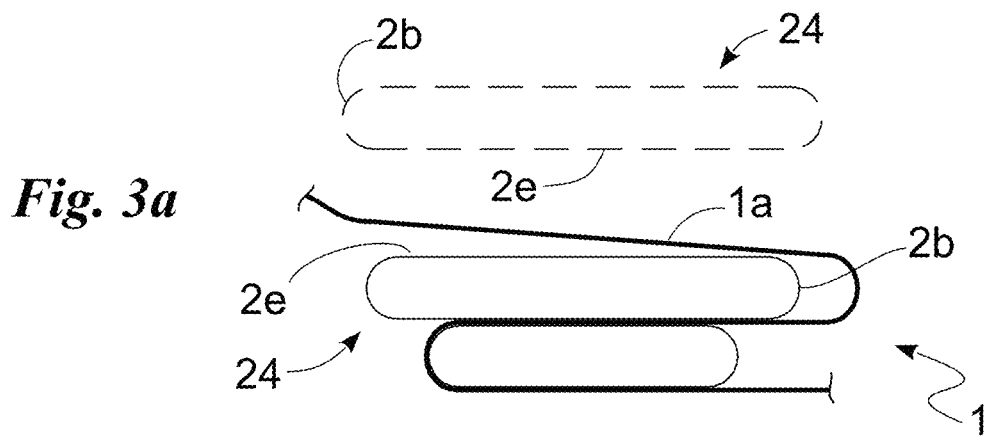
FIGS. 3a-3c show a further example of a diagnostic support for skins according to an embodiment of the present invention.
Figure 3B:
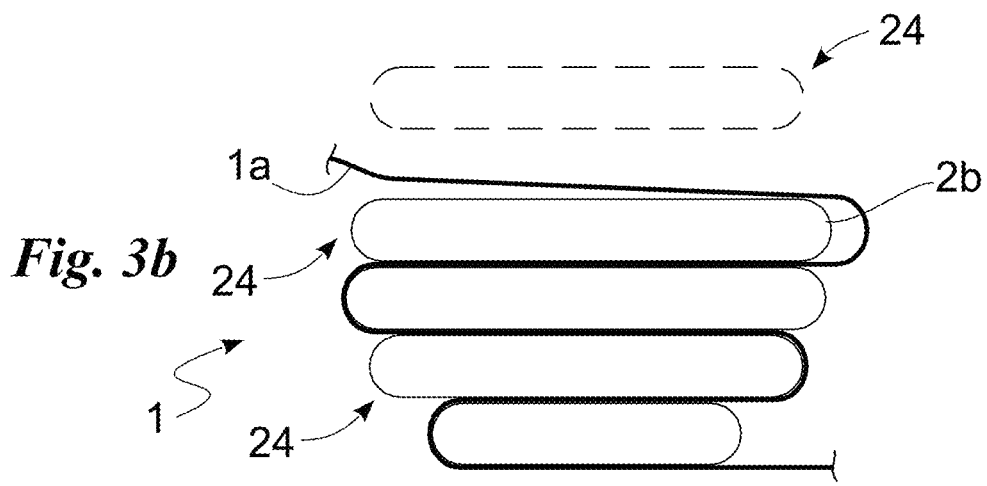
Figure 3C:
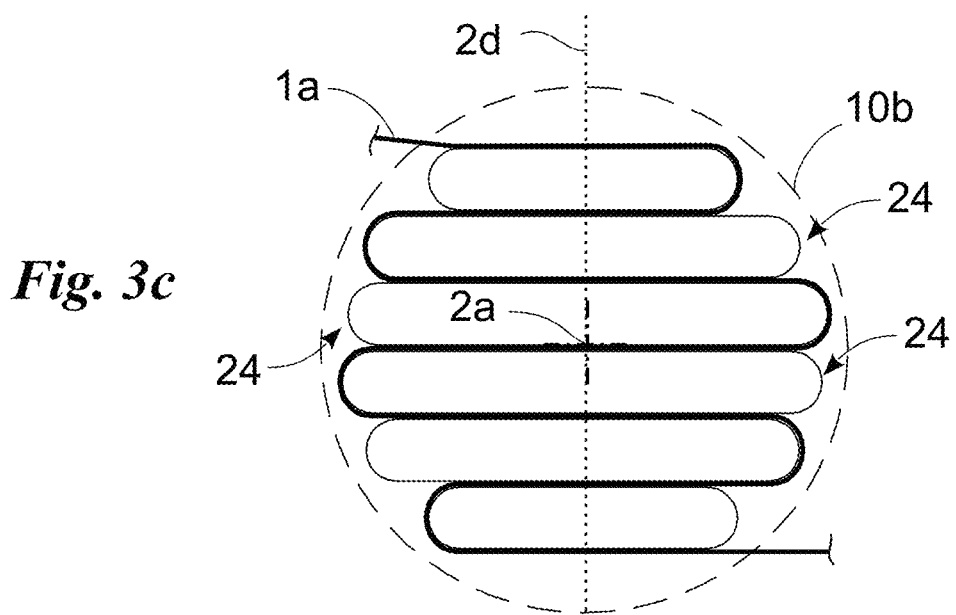

Another example of a multi-surface 2b radio-transparent structure 2 is shown in FIGS. 3a-3c showing a third preferred embodiment. In this case, the radio-transparent structure 2 may comprise a plurality of panels 24, preferably six, each defining a folding surface 2b and suitable to be stacked, thus arranging and folding the skin 1a. The panels 24 are suitable to be stacked, thereby placing the skin 1a between adjacent panels 24. Therefore, each panel 24 defines for the skin 1a at least one support surface 2e and one folding surface 2b. In particular, each panel defines two support surfaces 2e opposite to one another and connected by a single folding surface 2b. The support surfaces 2e of the panels 24 are parallel to each other and to the longitudinal axis 2a. In particular, they are perpendicular to the plane 2d. It should be noted that the width of the support surfaces 2e, calculated perpendicular to the plane 2d, of each panel 24 is inversely proportional to the axial distance of the panel 24 from the longitudinal axis 2a. The folding surface 2b may have a curved profile with a radius at least equal to 5 cm, and in detail equal to 10 cm. The panels 24 may have a length, measured along the longitudinal axis 2a, at least equal to that of the skin 1a, and in detail equal to 3 m. In order to support the panels 24, the diagnostic support 1 may comprise a support for the radio-transparent structure 2 identifiable, for example, as a known radiological bed.

Figure 4A:
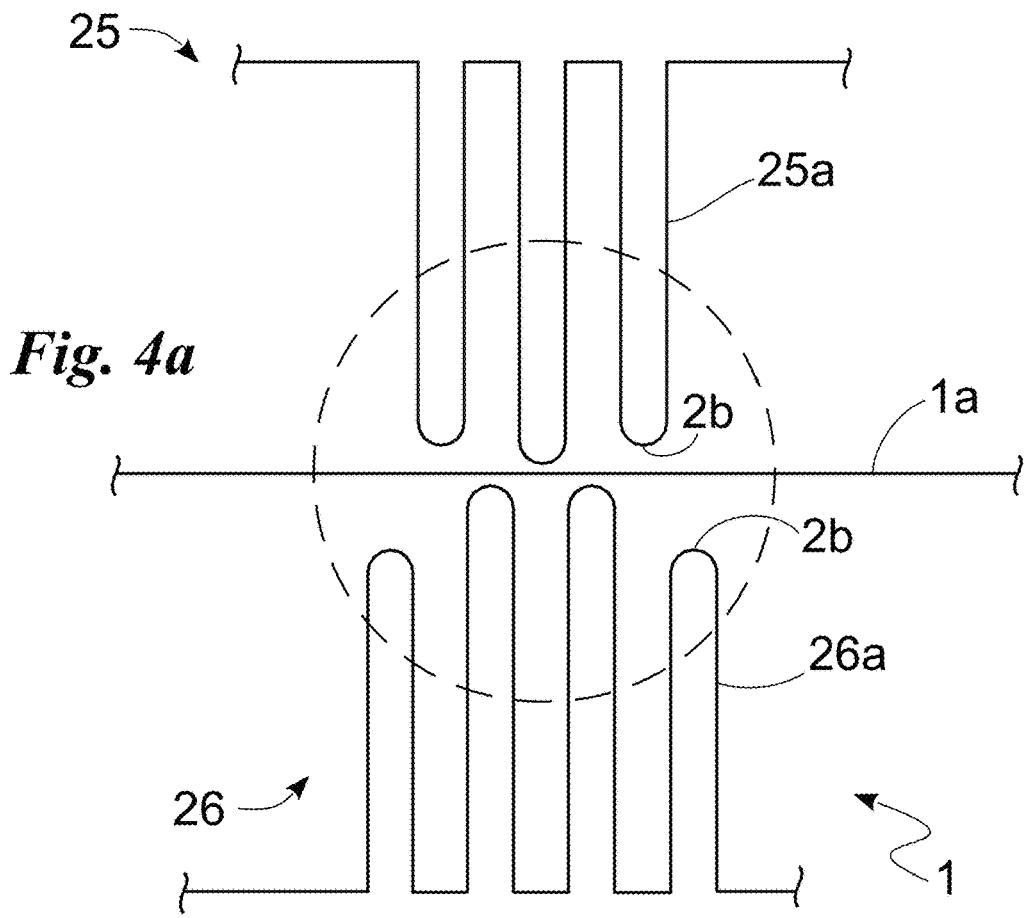
FIGS. 4a-4b show a further diagnostic support for skins according to an embodiment of the present invention.
Figure 4B:
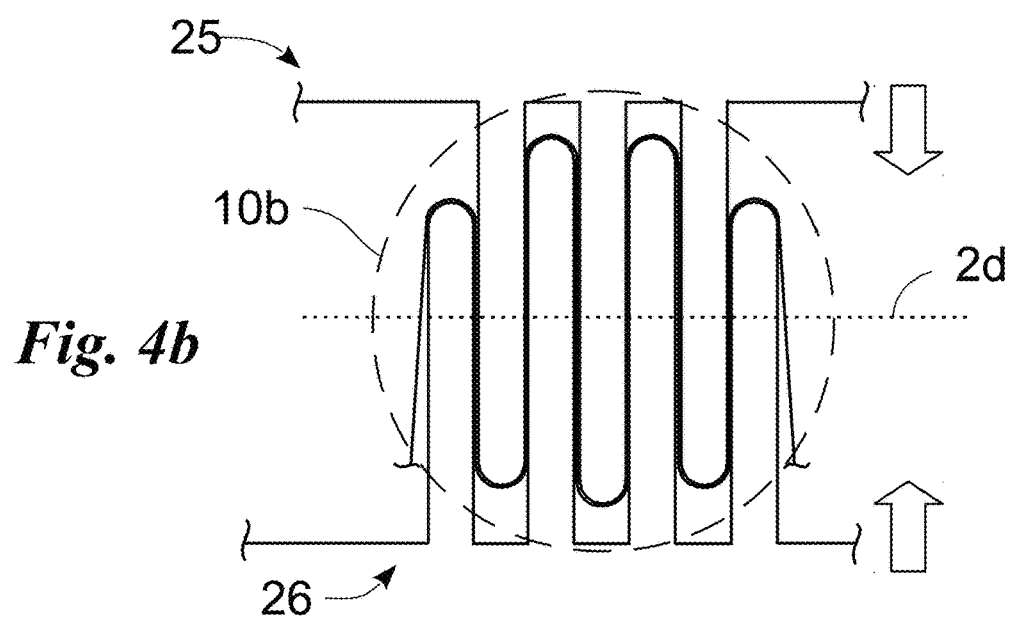

Another example of a multi-surface 2b structure 2 is shown in FIGS. 4a-4b showing a fourth preferred embodiment. In this case, the radio-transparent structure 2 comprises a first fork 25 comprising first tines 25a and a second fork 26 comprising second tines 26a suitable to position themselves between the first tines 25a, enabling the skin 1a to fit between the tines 25a and 26a by folding. The tines 25a and 26a are substantially parallel to each other. Their thickness, calculated perpendicular to the longitudinal plane 2d, is even so that the folded portions of the skin 1a are evenly spaced apart. This thickness is at least equal to 5 cm, and in detail equal to 10 cm. The tines 25a and 26a may have a length, measured along the longitudinal axis 2a, at least equal to that of the skin 1a, and in detail equal to 3 m. The projecting ends of the tines 25a and 26a define the folding surfaces 2b of the skin 1a and have a curved profile with a radius at least equal to 5 cm, and in detail equal to 10 cm.

In order to arrange and then fold the skin 1a between the tines 25a and 26a, the diagnostic support 1 may comprise a mover adapted to define a mutual motion of the forks 25 and 26 perpendicular to the longitudinal axis 2a. The mover defines an insertion position (FIG. 4a), in which the tines 25a and 26a are mutually spaced apart so as to allow the insertion of the skin 1a between the forks 25 and 26, and a folding position (FIG. 4b), in which the forks 25 and 26 are close together so as to mutually interpose the tines 25a and 26a, thereby folding the skin 1a. The diagnostic support 1 may comprise a conveyor adapted to move the skin 1a, arranging it between the tines 25a and 26a. The conveyor is identifiable as one or more wires integral with the skin 1a and adapted to slide between the tines 25a and 26a, dragging and, therefore, arranging the skin 1a between the tines 25a and 26a.

Finally, in each of the second, third, and fourth preferred embodiments, the diagnostic support 1 may comprise fastening means capable of bonding any loose flaps of the skin 1a to the radio-transparent structure 2. The fastening means are made of polyurethane foam or of a radio-transparent material.

Figure 5:
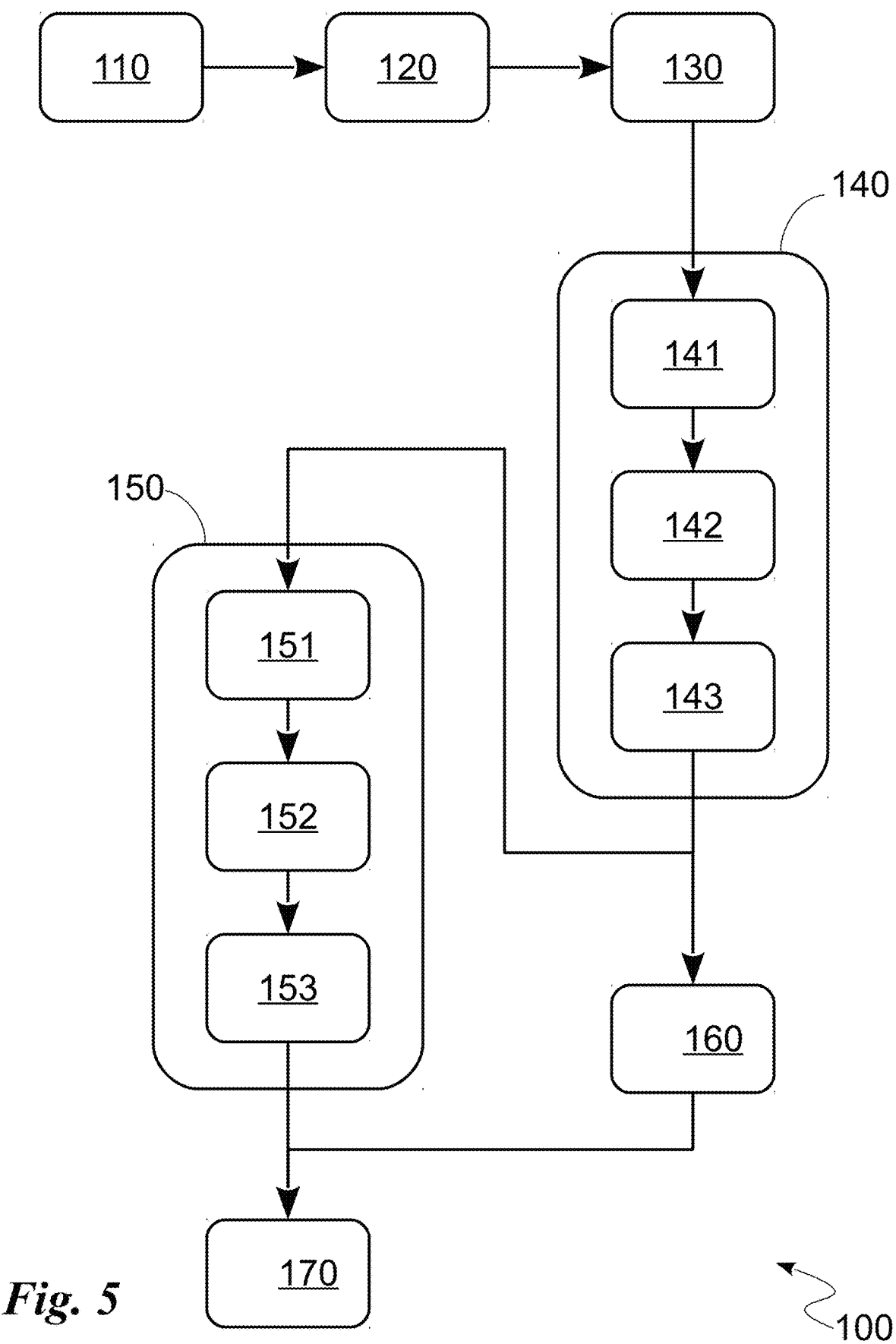
FIG. 5 shows a diagram of the method for inspecting a skin according to an embodiment of the present invention.

The analysis process can be part of a method for inspecting a skin 1a according to the invention generally designated by the reference numeral 100 and shown schematically in FIG. 5. The method 100 may be carried out by means of said apparatus for inspecting a skin 1a. It may also be implemented by means of the diagnostic support structurally described above.

Initially, the inspection method 100 may comprise a preparation step 110 wherein one or more of said markers (conveniently three) are associated with the skin 1a. Briefly, the inspection method 100 may comprise a first acquisition step 120 wherein said skin 1a is imaged at least once (preferably a radiological image and more preferably a tomography), a second acquisition step 130 wherein at least one superficial, specifically optical image of the skin 1a is obtained, and a relative orientation step 140 wherein the imaging and the superficial image are spatially cross-referenced so as to relate the points of the imaging to the points of the superficial image, making it possible to identify in the superficial image, and thus in the skin 1a, the position of a defect detected in the imaging. It should be noted that the first acquisition step 120 and the second acquisition step 130 may be carried out at the same time and/or at different times. The preparation step 110 may precede the acquisition steps 120 and 130 or be interposed between said acquisition steps 120 and 130.

In the first acquisition step 120, the imaging device 10 images at least part and preferably the whole skin 1a and, if present, the markers. The first acquisition step 120 may comprise, and precisely be carried out by using the diagnostic support 1 structurally described above. Therefore, it may comprise a folding sub-step wherein the skin 1a is folded so as to reduce the overall dimensions, and in particular the width thereof, a sub-step for inserting at least part of the folded skin 1a in the FOV 10b of an imaging device and suitably in an imaging device 10, and an acquisition sub-step wherein the folded skin 1a is imaged, thereby obtaining an image, in detail a radiological image and more in detail a tomography of the folded skin 1a.

In the folding sub-step, the skin 1a, by using the support 1, is folded back on itself, defining folded portions spaced apart, preferably at the same distance from each other. In detail, in the case of the support 1 of FIGS. 1a and 1b, at least part of the skin 1a is placed on the folding surface 2b by arranging the edge of the skin 1a in the fitting channel 2c. Preferably, the skin 1a is completely placed on the folding surface 2b. At this point, the flexible plate 21 and the skin 1a are folded on the base body 22, both of them taking on a spiral shape (FIG. 1b) and separating and suitably spacing evenly apart the folded portions of skin 1a.

Alternatively, in the case of the diagnostic support 1 of FIG. 2, the skin 1a is passed through the various sections 23 and rested on folding surfaces 2b alternated on opposite sides with respect to the longitudinal plane 1a.

In a further alternative (FIGS. 3a-3c), the skin 1a is placed on a support surface 2e of a first panel 24, folded on the folding surface 2b of the same first panel 24 and rested on the support surface 2e of the first panel 24 opposite to the preceding one. Now, a new panel 24 is rested on the skin 1a by enclosing it between the two panels. The skin 1a is folded on the folding surface 2b of the second panel 24 placed on a support surface 2 and the second panel 24. These operations are repeated until the entire skin 1a is folded on the panels 24.

In another alternative (FIGS. 4a and 4b), the skin 1a is positioned between the tines 25a and 26a so as to fold, thus defining folded portions separated from each other by the tines 25a and 26a, and suitably equally spaced apart. This operation is performed by placing the diagnostic support 1 in the insertion position, arranging the skin 1a between the forks 25 and 26 and then bringing the diagnostic support 1 in the folding position, i.e. bringing the forks 25 and 26 close together so as to mutually interpose the tines 25a and 26a, thus folding the skin 1a. Alternatively, this operation is performed by the conveyor which slides the skin 1a between the tines 25a and 26a.

Once the folding sub-step is finished, the insertion sub-step takes place, in which at least part of the skin 1a and of the radio-transparent structure 2 is placed in the FOV 10b, followed by the acquisition sub-step, wherein one or more acquisitions (for example at different angles) of at least part and suitably of the totality of the folded skin 1a is/are performed. The acquisition sub-step ends with the imaging, in detail, of a radiological image, and more in detail of a tomography of the folded skin 1a.

At this point, the first acquisition step 120 may comprise a stretching sub-step, wherein the imaging obtained in the acquisition sub-step is planarized, thus providing imaging of the stretched skin 1a. This stretching sub-step can be performed by planarizing a first surface, for example an edge, of the imaging of the skin 1a and replacing the pixels of the imaging on the basis of the coordinates and the distances of the pixels with respect to the first surface.

In the second acquisition step 130, the recording unit acquires a superficial (suitably optical) image of at least part of the skin 1a, and in detail of the exposed surface. Preferably, a superficial image of the whole exposed surface is obtained. Also a superficial image of the support surface, and in some cases of the lateral surface, may be acquired. The superficial image may comprise the markers. It should be noted that, both in the at least one superficial image and in the imaging, at least part of the perimeter of the skin 1a can be present.

Once the acquisition steps 120 and 130 are completed, the method 100 comprises the relative orientation step 140. The relative orientation step 140 may comprise a first identification sub-step 141 wherein at least a first discontinuity is detected in the imaging, a second identification sub-step 142 wherein at least a second discontinuity is detected in the superficial image, and a mutual cross-reference sub-step 143 wherein the imaging and the superficial image are mutually spatially referenced so as to relate the points or pixels of the imaging to the points or pixels of the superficial image, thereby allowing a localization of the defects in the skin 1a, and in particular the identification of the position of an internal defect, i.e. detected in the imaging, in the superficial image and then in the skin 1a. The term "point," as used herein, can be intended to mean individual pixels or a plurality of them. Preferably, the term "point" defines a single pixel.

The term "discontinuity" identifies a change in intensity between contiguous pixels greater than a predefined threshold and/or a geometric variation of the skin 1a in the imaging and/or in the superficial image. In particular, a discontinuity can be identified if the change in intensity between contiguous pixels is at least equal to a threshold of variation between the intensities of contiguous pixels. Such variation is at least equal to 1%, in detail equal to 5% and preferably equal to 10%. Alternatively, a discontinuity can be identified if the intensity of a pixel is less than a minimum acceptability threshold and/or greater than a maximum acceptability threshold. Geometric variation is identifiable in the case in which sudden changes in shape, such as those found at the perimeter of the skin 1a, or of one or more markers characterized by a peculiar profile/shape, are detected in the imaging and/or in the superficial image. Therefore, a discontinuity can be detected at the profile of the skin 1a and/or of the markers. Alternatively or additionally, a discontinuity can be detected in the area of one or more defects visible in the imaging (in particular in the radiological image) and in the superficial image. Further alternatively or additionally, a discontinuity can be detected in the area of a hole or other reference specially provided in the skin 1a before inspection.

After identifying first and second discontinuities, the sub-steps 141 and 142 are concluded and the mutual cross-reference sub-step 143 begins, in which, by causing at least a first discontinuity to coincide with at least a second discontinuity, the imaging and the superficial image are mutually spatially referenced so as to be able to link any point or pixel of the imaging to a point or pixel of the superficial image, and therefore of the skin 1a. The reference between the imaging and the superficial image is obtainable by causing one or more first discontinuities to match to, and precisely to coincide with, one or more second discontinuities. This operation can be performed by causing the profile of one or more first discontinuities to coincide with the profile of one or more second discontinuities. In particular, first and second discontinuities identifiable at the perimeter of the skin 1a and/or related to the shape of a marker can be used. Alternatively, reference between the acquired images is obtained by causing the position of two or more first discontinuities of the imaging to coincide with two or more second discontinuities of the superficial image. It should be noted that, for greater precision, these acquired images of a skin 1a may be mutually referenced by causing both the profile and the position of first and second discontinuities to coincide.

At this point, the mutual cross-reference sub-step 143 and the relative orientation step 140 are concluded and the inspection method 100 may comprise a, preferably automatic, identification step 150, for detecting skin 1a defects in said skin 1a on the basis of the first and second discontinuities and/or a step 160 for linking the imaging to the superficial image.

The identification step 150 comprises, initially, a cross-reference sub-step 151 wherein a cross-reference system common to said imaging and to said image is identified and with respect to which the first and second discontinuities can be referred. The reference system can be determined by making use of the first and second discontinuities used in the cross-reference sub-step 143, for instance, by arranging the origin of said reference system at a point common to the first and second discontinuities. In particular, the reference system may have two parallel axes and one axis perpendicular to the exposed surface of the skin 1a.

Thus, the identification step 150 comprises a localization sub-step 152 in which the coordinates defining the position, and in some cases the shape, of the discontinuities and, therefore, of the defects are determined with respect to the reference system. In this localization sub-step 152, first coordinates defining the position of the first discontinuity in the imaging with respect to the reference system are determined for each first discontinuity, and second coordinates defining the position of the second discontinuity in the superficial image with respect to the reference system are determined for each second discontinuity. Additionally, the first coordinates may define the shape of the first discontinuities, and the second coordinates may define the shape of the second discontinuities. The identification step 150 may comprise a data collection sub-step 153 in which a defects database is created, which links the first and second coordinates to each defect detected in the imaging and in the superficial image as described above. In the linking step 160, the spatial reference between the imaging and the superficial image can be used to generate a composite image of the imaging and the superficial image, which allows the passage, during a visualization, from the imaging to the superficial image or vice versa without changing the orientation of the skin 1a.

Lastly, the inspection method 100 may comprise a step of removing 170 the detected defects from the skin 1a on the basis of the first and second coordinates of the defects, and in detail on the basis of the defects database. In this step, the removal can be performed by the removal device which, on the basis of the defects database, is able to automatically locate and remove the defects present in the skin 1a.

The above described inspection method 100 and specifically the first acquisition step 120 teach a new use of a diagnostic support for folding a skin 1a on the diagnostic support 1, reducing the width of the skin 1a to a value that is substantially smaller than the diameter of the FOV 10b of an imaging device, thereby allowing at least a partial introduction of the skin 1a, which is folded on the diagnostic support 1, in the FOV 10b.

This new use of the diagnostic support allows the skin 1a to be folded, thus defining folded portions of said skin 1a that are not in contact with each other. In detail, the use of the diagnostic support 1 defines folded portions of the skin 1a that are equally spaced from one another, and more in detail substantially parallel to each other. The invention provides significant advantages.

A first important advantage is that the diagnostic support 1 and the method 100 allow the execution of an objective analysis of the defects present within the skin, and therefore allow a uniformity of evaluation of the skin 1a, until now impossible. An important advantage is that the inspection method 100, by spatially cross-referencing the imaging and the superficial image, allows all the defects present on the skin 1a to be identified in an extremely precise manner. An important advantage is that the cross-referencing of the imaging and the superficial image can be performed without performing any operations (such as dyeing) on the skin 1a, which until now are normally performed and make some portions of the skin 1a unusable.

Another advantage is that the inspection method 100 allows the position, size, and shape of all the defects present in the skin 1a to be identified in a very precise way, thus allowing the reduction of the extent of the skin 1a to be removed in order to remove the defect. Another advantage lies in the fact that the inspection method 100 minimizes the discarded parts, and therefore the manufacturing price of a skin 1a.

A no less important advantage is given by the composite image, which allows the passage from the imaging to the superficial image or vice versa without changing the orientation of the skin 1a. Therefore, the operator may, for example, visualize a defect in the superficial image and switch to the imaging to obtain the depth of the superficially identified defect or, alternatively, locate an internal defect in the imaging and then switch to the superficial image to accurately determine its position.

Another important advantage lies in the fact that the diagnostic support 1, the method, and the use defined thereby allow the overall dimensions of the skin 1a to be reduced, allowing it to be inserted within an FOV 10b of any of the imaging devices 10 known to date. A major advantage is also to be found in the fact that the diagnostic support separates the folded portions of the skin 1a, thus favoring the identification of defects.

The invention is susceptible of variations falling within the scope of the inventive concept, as specified in the independent claims, and of the related technical equivalents. In this context, all details are replaceable by equivalent elements and any type of materials, shapes and dimensions may be present. In particular, in the superimposing sub-step 143, the spatial reference between the imaging and the superficial image can be carried out by using the information relating to the mutual position between the imaging device and surface recording unit.

The invention claimed is:

1. A method for inspecting a skin designed to detect defects in said skin, comprising:
    obtaining a radiological image of said skin, wherein said radiological image comprises a plurality of pixels;
    storing said radiological image in a memory;
    obtaining a superficial image of said skin, wherein said superficial image comprises a plurality of pixels and said skin comprises at least one bonded marker that is optical and radio-opaque;
    storing said superficial image in the memory; and
    spatially cross-referencing said radiological image and said superficial image, wherein said spatial cross-referencing comprises:
        retrieving said radiological image from the memory;
        detecting at least a first discontinuity in said radiological image;
        retrieving said superficial image from the memory;
        detecting at least a second discontinuity in said superficial image; and
        spatially cross-referencing said radiological image and said superficial image by matching at least one of said at least first discontinuity to at least one of said at least second discontinuity.

2. The method according to claim 1, further comprising:
    defining a cross-reference system common to said radiological image and to said superficial image with respect to which said first discontinuities and said second discontinuities can be referred; and
    detecting a location of said defects in said skin on the basis of said first and second discontinuities.

3. The method according to claim 2, further comprising determining first coordinates of said first discontinuities in said radiological image and second coordinates of said second discontinuities in said superficial image,
    wherein said determined first coordinates define a position of said defects in said radiological image, and said determined second coordinates define a position of said defects in said superficial image.

4. The method according to claim 3, further comprising defining a defects database that associates each of said defects in said skin with said first and second coordinates.

5. The method according to claim 4, wherein said defects database associates a form of said defect to each of said defects and the method further comprises removing said defects from said skin based on said defects database.

6. The method according to claim 1, wherein said radiological image is obtained using tomography.

7. A method for inspecting a skin designed to detect defects in said skin, comprising:
    obtaining a radiological image of said skin, wherein said radiological image comprises a plurality of pixels;
    storing said radiological image in a memory;
    obtaining a superficial image of said skin, wherein said superficial image comprises a plurality of pixels;
    storing said superficial image in the memory; and
    spatially cross-referencing said radiological image and said superficial image, wherein said spatially cross-referencing comprises:
        retrieving said radiological image from the memory;
        detecting at least two first discontinuities in said radiological image;
        retrieving said superficial image from the memory;
        detecting at least two second discontinuities in said superficial image; and
        spatially cross-referencing said radiological image and said superficial image by causing the positions of the at least two first discontinuities to coincide with the positions of the at least two second discontinuities.

8. The method according to claim 7, further comprising:
    defining a cross-reference system common to said radiological image and to said superficial image with respect to which said first discontinuities and said second discontinuities can be referred; and
    detecting a location of said defects in said skin on the basis of said first and second discontinuities.

9. The method according to claim 8, further comprising determining first coordinates of said first discontinuities in said radiological image and second coordinates of said second discontinuities in said superficial image,
    wherein said determined first coordinates define a position of said defects in said radiological image, and said determined second coordinates define a position of said defects in said superficial image.

10. The method according to claim 9, further comprising defining a defects database that associates each of said defects in said skin with said first and second coordinates.

11. The method according to claim 10, wherein said defects database associates a form of said defect to each of said defects and the method further comprises removing said defects from said skin based on said defects database.

12. The method according to claim 7, wherein said radiological image is obtained using tomography.

* * * * *

UNITED STATES PATENT AND TRADEMARK OFFICE
CERTIFICATE OF CORRECTION

| | | |
|---|---|---|
| PATENT NO. | : 11,199,531 B2 | Page 1 of 1 |
| APPLICATION NO. | : 16/098846 | |
| DATED | : December 14, 2021 | |
| INVENTOR(S) | : Fortuna et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 108 days.

Signed and Sealed this
Twenty-seventh Day of September, 2022

Katherine Kelly Vidal
*Director of the United States Patent and Trademark Office*